United States Patent [19]

Intlekofer et al.

[11] Patent Number: 4,858,810
[45] Date of Patent: Aug. 22, 1989

[54] QUICK ACTING PIN VISE FOR USE WITH ANGIOGRAPHIC GUIDEWIRES

[75] Inventors: Michael J. Intlekofer, Bellevue; Michael W. Slota, Bothell, both of Wash.

[73] Assignee: Heart Technology, Inc., Redmond, Wash.

[21] Appl. No.: 44,172

[22] Filed: Apr. 30, 1987

[51] Int. Cl.⁴ .................. A61B 17/00; B65H 20/00
[52] U.S. Cl. ............................ 226/127; 24/115 M; 24/136 R; 128/303 R; 604/159
[58] Field of Search ............ 24/115 R, 115 F, 115 G, 24/115 M, 136 R; 128/303 R, 772; 226/158, 162, 127; 254/134.3 R, 134.3 FT; 604/159

[56] References Cited

U.S. PATENT DOCUMENTS

| 904,863 | 11/1908 | Glass et al. | 24/136 R |
|---|---|---|---|
| 1,238,167 | 8/1917 | McIntyre | 24/136 R |
| 1,442,862 | 1/1923 | Curtis | 24/136 R |
| 2,220,203 | 11/1940 | Branin | 24/136 R |
| 2,625,934 | 1/1953 | Halliday | 128/303 R |
| 3,070,057 | 12/1962 | Dezzani | 226/158 |
| 3,312,128 | 4/1967 | Wasson | 254/134.3 R |
| 4,598,708 | 7/1986 | Beranek | 128/303 R |
| 4,726,369 | 2/1988 | Mar | 128/303 R |

Primary Examiner—Dalton L. Truluck

[57] ABSTRACT

The pin vise is usable in connection with guidewire of the type used in medical applications, i.e., for guiding catheters. The pin vise is constructed from two parts which are assembled together to provide a handle over a guidewire.

7 Claims, 4 Drawing Sheets

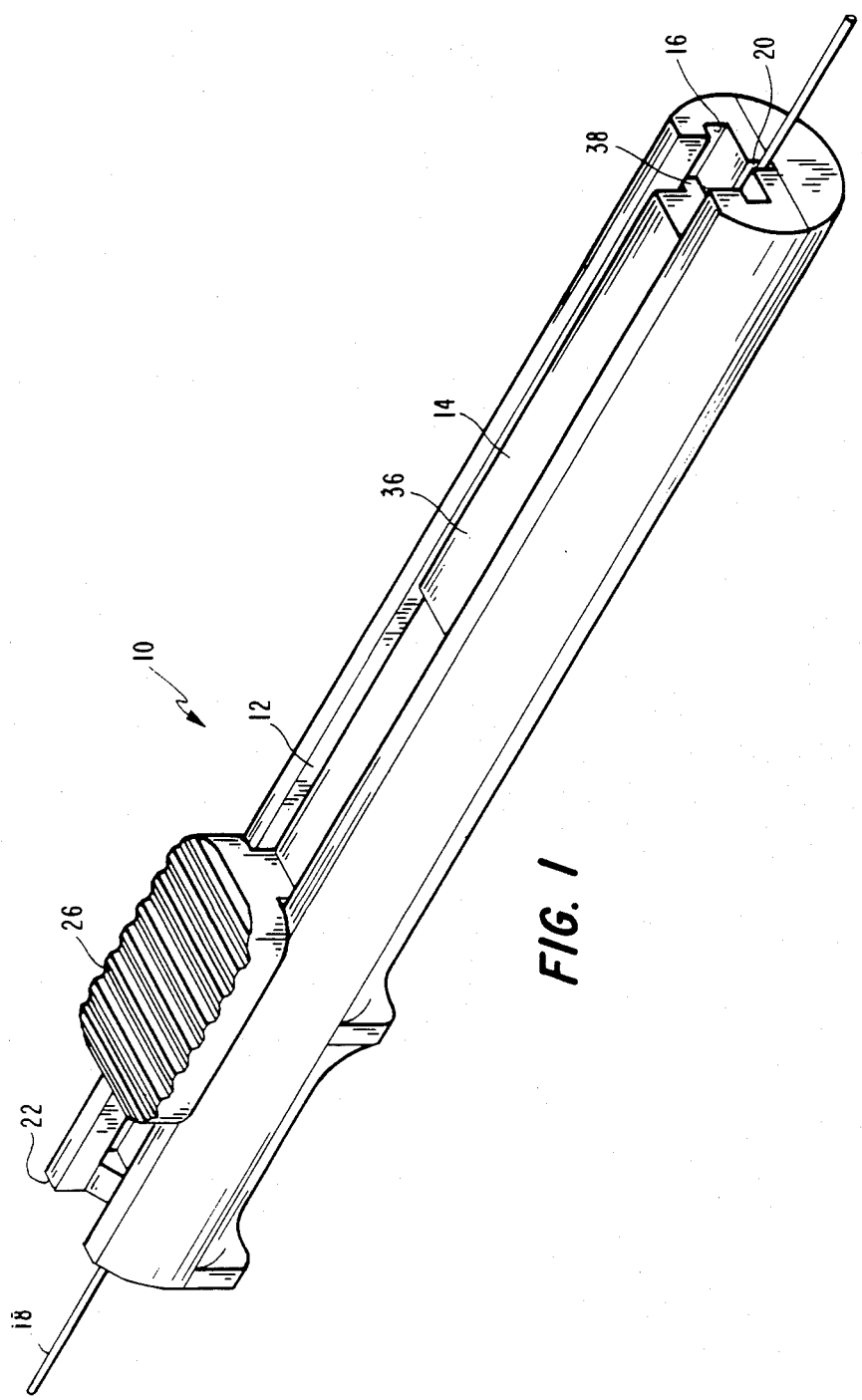

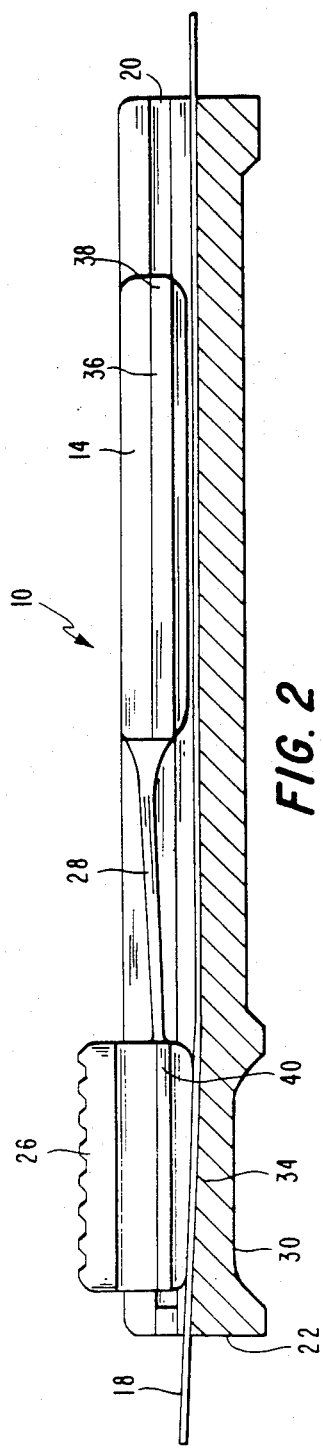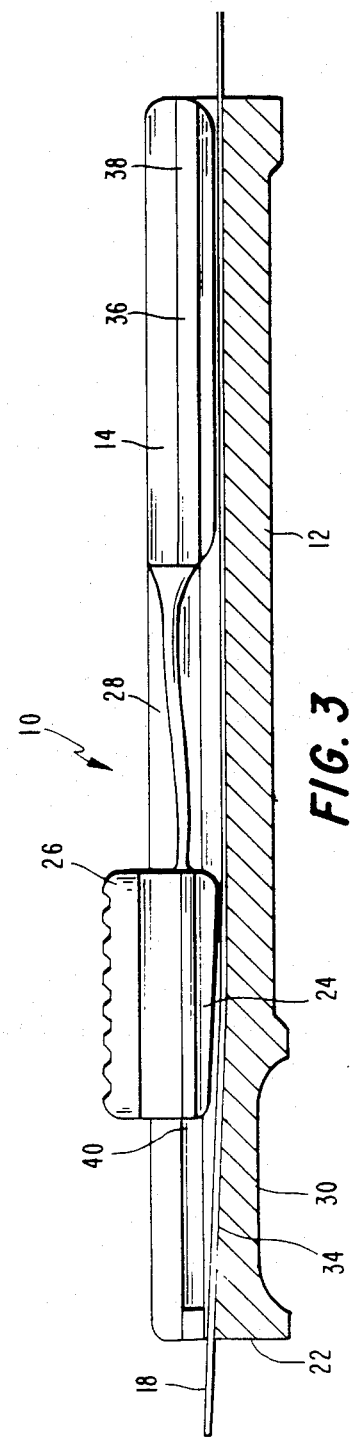

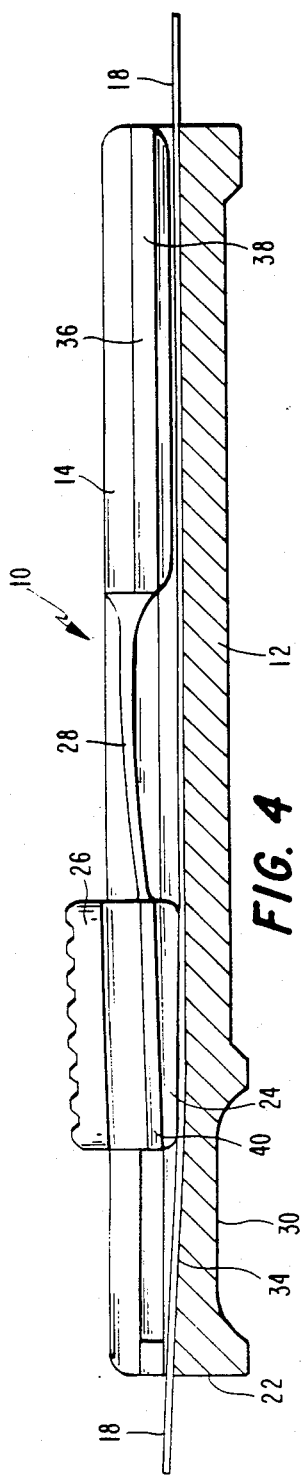
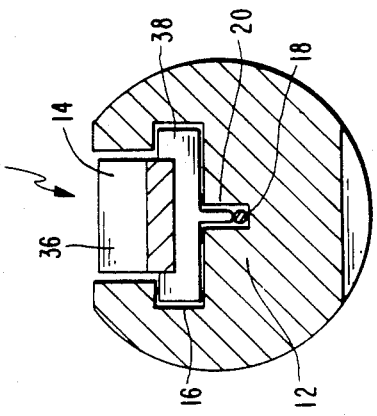
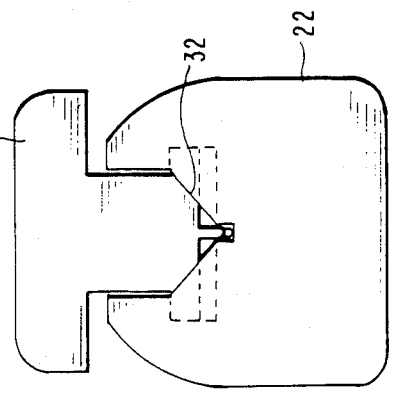

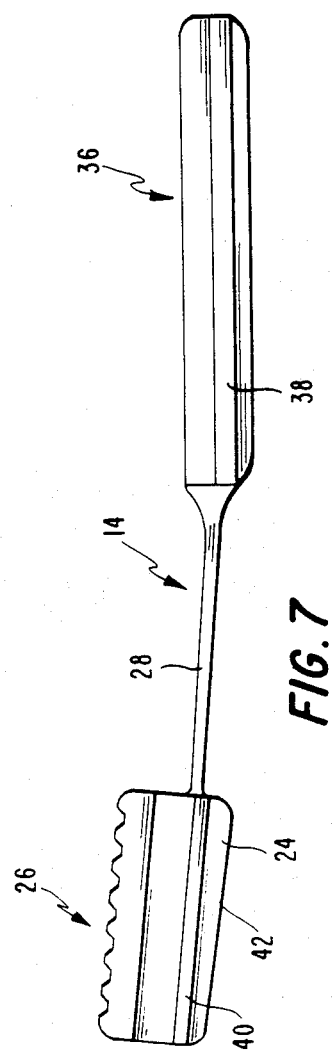

QUICK ACTING PIN VISE FOR USE WITH ANGIOGRAPHIC GUIDEWIRES

The present invention relates to a device which may be attached to a wire in order to permit one to turn the wire comfortably. In particular, the device relates to a pin vise.

BACKGROUND OF THE INVENTION

Modern angiographic practice calls for the extensive use of guidewires during the catheterization of human arteries and arterial branches. A typical steerable guide wire consists of a flexible distal section, usually a spring, connected to a long slender section of wire or tubing which is manipulated for axial advancement and retraction, and rotational torque transmission. This combination of features allows the guidewire to negotiate through the compound curves involved in the human arterial system, and when finally in place, to act as a guide for flexible diagnostic and therapeutic catheters which are slipped over it.

Since the proximal ends of the guidewires are typically small diameter wire or tubing (often hard-drawn stainless steel) and have a hard, polished, surface, they are very difficult to grasp securely. Medical device manufacturers currently provide a variety of so-called "pin vises", or "torquers", or "handles" which are intended to grip and manipulate the wires, but they all suffer from one or more deficiencies.

SUMMARY OF THE INVENTION

The present invention is a pin vise which may be attached to a medical guidewire. The pin vise comprises an elongated, cylindrical body portion having a slot whose cross-section is shaped to receive a guidewire and a means for holding said guidewire. It also comprises a slider portion adapted to be received within the the elongated slot in the body portion. The slider portion includes means for moving the slider portion and means for holding the guidewire. The means for holding said guidewire is adapted to frictionally coact with the guidewire and with the body portion.

BRIEF DESCRIPTION OF THE DRAWING

FIG. 1 is a perspective view of the pin vise of the present invention;

FIG. 2 is a longitudinal section of the pin vise of FIG. 1 with the slider attached to a guidewire;

FIG. 3 is a longitudinal section of the pin vise of FIG. 1 with the bottom of the slider just contacting the guidewire;

FIG. 4 is a longitudinal section of the pin vise of FIG. 1 with the thumbpiece of the slider depressed;

FIG. 5 is a front view of the pin vise of the present invention;

FIG. 6 is a cross-sectional view of the pin vise of the present invention; and

FIG. 7 is a detailed view of the slider.

DETAILED DESCRIPTION OF THE PREFERRED EMBODIMENT

Referring generally to FIG. 1, the pin vise 10 of the preferred embodiment is made of a lightweight, sterilizable plastic, such as Ultem TM, making it ideally suited to use as disposable medical device.

The pin vise 10 is comprised of two parts, the body 12 and the slider 14, which separate for side mount applications, and which mate using an arrangement employing a T-slot 16 (shown in cross section in FIG. 6). The T-slot 16 runs the entire length of the body 12, it accommodates the slider 14, and it provides the structure necessary to oppose the clamp forces when a wire 18 (see FIG. 4) is being gripped. In the bottom of the T-slot 16 is a groove 20, which runs at a fixed depth for most of its length, but inclines upward near the front 22 of the body 12. This incline is the site where the wire 18 is wedged by a wedge blade 24 on a thumbpiece 26 of the slider 14. The widths of the groove 20 and blade 24 are chosen to accommodate a variety of commercial guide wire sizes. By way of example, they will accommodate a 0.009" diameter guide wire.

The thumbpiece 26 protrudes above the body 12 and is used to advance or retract the slider 14. The thumbpiece 26 acts also as a pushbutton when the pin vise 10 is used in the "inching" mode described below. The thumbpiece 26 is joined to the block via a spring 28 comprised of a thin, limber segment of plastic or metal which has a preformed curve formed into it.

The spring 28 serves two purposes. It provides a constant frictional drag between the slider 14 and the body 12 in order to prevent the slider 14 from falling out of the body 12 during handling. The frictional drag is imposed when the naturally curved slider 14 is inserted into the body 12, where it is forced to follow the T-slot groove 16 and assume a straight, rather than a curved configuration. It acts as a flexible hinge when the pin vise 10 is used in the "inch" mode as explained below. In this situation, the thumbpiece 26 is positioned at some distance from the front end 22 of the pin vise 10, and pressed down or released in order to grip the wire 18 in a momentary fashion.

The pin vise body 12 is substantially cylindrical in shape, and has a surface finish on its bottom which provides a secure grip in the hand even in the presence of blood, saline or contrast agents. A finger stop 30 is provided at the front to prevent slippage and to overcome any tendency of the device 10 to roll when placed on an inclined surface. The finger stop 30 allows the user to identify the front of the unit 10 udner subdued light conditions, such as exist in the typical angio suite. A "V-notch" opening 32 on the front 22 of the unit 10 aids in wire loading and prevents inadvertent loading of the slider 14 from the wrong end.

The guidewire is either end loaded or side loaded. When the guidewire is end loaded, the thumbpiece 26 is moved back to a point about 1 cm from the front 22 of the body 12, and released. The end of the wire 18 is placed in the groove 18 ahead of the thumbpiece 26 and advanced so as to pass under the thumbpiece 26 and block and extend from the end of the pin vise 10. The end of the wire 18 can then be grasped and the pin vise 10 slid down to the point of use.

When the guidewire 18 is side loaded, the slider 14 is removed from the body 12, and set aside. The body 12 is placed adjacent to the wire 18 at the point of use, and the wire 18 is gently guided into the groove 20 along the entire length of the body 12. The slider 14 is then inserted into the body 12 and advanced to the operating position.

The pin vise has two modes of operation, the "lock" mode and the "inch" mode. In the "lock" mode, the wire 18 is inserted by either of the above two methods, and the pin vise 10 is positioned on the wire 18 at the point of use. At this point, the configuration of the pin vise 10 is as shown in FIG. 3, and since the blade 24 below the thumbpiece 26 is not in contact with the wire 18, the wire 18 is free to move and the pin vise 10 is in the released position. Now the thumbpiece 26 is advanced towards the front 22 of the pin vise 10, and the incline of the blade binds the wire 18 against the incline 34 in the body 12, as shown in FIG. 2. When the thumbpiece 26 is pressed firmly forwards, it locks by friction in the forward position and securely grips the wire 18. The pin vise 10 can now be advanced, retracted, and rotated to manipulate the guidewire 18 as necessary. Since the grip is locked, it is not necessary to maintain pressure on the thumbpiece 26 while rotating the pin vise 10. This is a significant feature for user convenience. The thumbpiece 26 can be moved forward and back to grip and release the wire 18 as necessary during the procedure.

In the "inch" mode, the wire is inserted by either of the previously described two methods, and the pin vise 10 is positioned at the point of use. At this point, the configuration of the pin vise 10 is as shown in FIG. 3, and since the blade 24 below the thumbpiece 26 is not in contact with the wire 18, the wire 18 is free to move, and the pin vise 10 is in the released position. Now the thumbpiece 26 is depressed (not advanced) to grip the wire in a momentary fashion, so the wire can be advanced incrementally, an inch or so at a time. After the wire 18 is advanced, the thumbpiece 26 depressed again, and so on. Using this method, a guidewire 18 can be advanced readily, even against resistance, without risk.

In the preferred embodiment of the invention, the slider 14 is a one piece unit, preferably molded, and the spring 28 is between the block 36 and the thumbpiece 26 precurved as shown in FIG. 7. When the slider 14 is inserted into the body 12, the spring 28 is forced into a nearly straight configuration. Since the block 36 is relatively long, and its "T" 38 matches the body "T" closely, the spring 28 tends to use the block 36 as a reference, and attempts to lift the thumbpiece 26 in the T-slot 16. Since the thumbpiece "T" 40 is made thinner in section than the body "T" 38, it has clearance beneath, as shown in FIG. 5, which allows it to act as spring-return pushbutton in the "inch" mode. The spring 28 must be carefully designed to give the proper return force to the thumbpiece 26 for best operator feel. If molded of Ultem, which has a modulus of 430,000 psi, a beam deflection calculation shows that a spring 1" long 1" long×0.180" wide and 0.037" thick, with a preformed offset of 0.100" would have a deflection force of approximately 45 grams. This valve would give a suitable return force. In practice, a tapered, or a "wasp waist" spring shape could be used for minimum material and optimum strain distribution considerations.

In the preferred embodiment of the invention, the incline 34 on the body 12 (as shown in FIG. 2) and the incline 42 on the thumbpiece 26 (as shown in FIG. 7) are approximately 2.5 degrees. These valves give the proper wedging and gripping action on a stainless steel guidewire 18 over a wide range of sizes, exploiting the coefficient of friction between Ultem ™ and stainless (about 0.45) and at the same time insures that the thumbpiece 26 will stick in the "lock" mode when firmly advanced against the wire 18, exploiting the coefficient of friction between Ultem ™ and Ultem ™ (about 0.45).

I claim:

1. A pin vise which may be attached to a medical guidewire comprising:

an elongated, cylindrical body portion having a slot which runs substantially parallel to the axis of said cylindrical body portion whose cross-section is shaped to receive a guidewire and a means for holding said guidewire, said slot comprising a first slot portion which opens to ambient atmosphere through an elongated side of said body portion; a slot portion transverse to said first slot portion and a groove in communication with said first and transverse slot portions, said groove having a much narrower cross-section than either said first or transverse slot portion and being adapted to receive said guidewire; and a plastic slider portion adapted to be received within said slot and slidable back and forth therein, between a remote position and a lock position, said slider portion including:

means for moving said slider portion;

means for holding said guidewire further comprising a narrow blade extending into said groove for frictional engagement with said guidewire as said slider portion is moved toward said lock position; and means for retaining said slider portion within said body portion when said holding means is not engaging a guidewire.

2. The pin vise of claim 1 wherein said retaining means comprises a block portion coupled to said holding means by a precurved elongated spring, said holding means and block portion comprising flange means for engagement with said transverse slot portion, said coupled holding means, spring and block portion biasing said holding means and block portion into frictional engagement with said transverse slot portion.

3. The pin vise of claim 1 wherein said slider portion comprises means for inching said guidewire through said cylindrical body portion.

4. The pin vise of claim 3 wherein said groove is sloped toward said transverse slot portion at said lock position and said blade is disposed to gradually engage a guidewire as the holding means is moved toward said lock position when a guidewire is present in said groove.

5. The pin vise of claim 4 wherein said inching means comprises a block portion coupled to said holding means by a precurved elongated spring, said holding means and block portion comprising flange means disposed within said transverse slot portion, said spring and block portion biasing said holding portion flange means into engagement with said transverse slot portion away from said groove, said holding portion being movable up and down within said transverse slot portion intermediate said remote and lock positions when pressure is applied to said slider portion moving means, said holding means movable toward and away from said block portion when said slider portion is in said intermediate position and engagable with a guidewire present in said groove whereby said guidewire can be engaged and inched forward through said cylindrical body portion as often as desired.

6. The pin vise of claim 5 wherein said blade is sloped away from said groove, said slope being substantially the same as the slope in said groove at said lock position.

7. The pin vise of claim 5 wherein said holding means comprises a block portion adpated to slide along said first slot portion, said blade extending away from a first side of said block portion and wherein said moving means comprises a thumbpiece attached to a side of said block portion opposite said first side and extending above said cylindrical body portion.

* * * * *